US011281203B2

(12) United States Patent
Cussonneau et al.

(10) Patent No.: US 11,281,203 B2
(45) Date of Patent: Mar. 22, 2022

(54) METHOD FOR DETECTING ANOMALIES IN A WATER DISTRIBUTION SYSTEM

(71) Applicant: SUEZ GROUPE, Paris la Défense (FR)

(72) Inventors: Guillaume Cussonneau, Paris (FR); Pierre-Antoine Jarrige, Montesson (FR); Abel Dembele, Villeurbanne (FR); Francis Campan, Antony (FR)

(73) Assignee: SUEZ GROUPE, Paris la Défense (FR)

( * ) Notice: Subject to any disclaimer, the term of this patent is extended or adjusted under 35 U.S.C. 154(b) by 1078 days.

(21) Appl. No.: 15/737,704

(22) PCT Filed: Jun. 29, 2016

(86) PCT No.: PCT/EP2016/065212
§ 371 (c)(1),
(2) Date: Dec. 18, 2017

(87) PCT Pub. No.: WO2017/001522
PCT Pub. Date: Jan. 5, 2017

(65) Prior Publication Data
US 2018/0181111 A1    Jun. 28, 2018

(30) Foreign Application Priority Data

Jun. 29, 2015 (EP) .................................. 15306029

(51) Int. Cl.
*G05B 23/02* (2006.01)
*G05B 13/04* (2006.01)
(Continued)

(52) U.S. Cl.
CPC ..... *G05B 23/0259* (2013.01); *G05B 13/0265* (2013.01); *G05B 13/04* (2013.01);
(Continued)

(58) Field of Classification Search
CPC ......... G06F 30/20; G05B 17/02; G05B 13/04; G05B 13/0265; G05B 13/041; G05B 13/048
(Continued)

(56) References Cited

U.S. PATENT DOCUMENTS 8,635,051 B1    1/2014  Wu et al.
2003/0093236 A1*  5/2003  Wu .......................... G06N 3/126
                                                                        702/85
(Continued)

FOREIGN PATENT DOCUMENTS

CN        1760912 A      4/2006
CN      103472820 A     12/2013
(Continued)

OTHER PUBLICATIONS

O. Piller et al., "Dual Calibration for Coupled Flow and Transport Models of Water Distribution Systems," Water Distribution Systems Analysis WDSA Dec. 2010, pp. 722-731.
(Continued)

Primary Examiner — Jigneshkumar C Patel
(74) Attorney, Agent, or Firm — BakerHostetler

(57) ABSTRACT

A method and a system for detecting anomalies in a water distribution system comprises a network of nodes, and is equipped with sensors of at least water velocity at a subset of the nodes. The water distribution system is modeled by a hydraulic model. The method comprises parametrizing the hydraulic model with initial values of a set of control variables, using the sensors to obtain values of state variables of the network at the nodes, using the hydraulic model to calculate predicted values of state variables, recursively calculating the values of control variables which, applied to the hydraulic model, permit to obtain the predicted values of state variables the closest to the observed values, and (Continued)

classifying nodes of the network based on the values of control variables.

16 Claims, 6 Drawing Sheets

(51) Int. Cl.

| | | |
|---|---|---|
| *G05B 17/02* | (2006.01) | |
| *G05B 13/02* | (2006.01) | |
| *G06N 20/00* | (2019.01) | |
| *G06F 30/20* | (2020.01) | |
| *G06N 7/00* | (2006.01) | |
| *G06Q 50/06* | (2012.01) | |
| *G01N 33/18* | (2006.01) | |
| *G06F 111/10* | (2020.01) | |

(52) U.S. Cl.
CPC ......... *G05B 13/041* (2013.01); *G05B 13/048* (2013.01); *G05B 17/02* (2013.01); *G06F 30/20* (2020.01); *G06N 7/005* (2013.01); *G06N 20/00* (2019.01); *G01N 33/18* (2013.01); *G06F 2111/10* (2020.01); *G06Q 50/06* (2013.01)

(58) Field of Classification Search
USPC .......................................................... 700/29
See application file for complete search history.

(56) References Cited

U.S. PATENT DOCUMENTS

2013/0262068 A1* 10/2013 Israeli .................. F17D 5/02
703/9
2014/0052421 A1 2/2014 Allen et al.
2014/0163916 A1 6/2014 Ba et al.

FOREIGN PATENT DOCUMENTS

| WO | 2010/131001 A1 | 11/2010 | |
|---|---|---|---|
| WO | WO-2010131001 A1 * | 11/2010 | .............. G01M 3/26 |
| WO | 2013/026731 A1 | 2/2013 | |
| WO | 2017001523 A1 | 1/2017 | |

OTHER PUBLICATIONS

Piller, "Modeling the behavior of a network—Hydraulic analysis and sampling procedures for parameter estimation", Applied Mathematics thesis from the University of Bordeaux (PRES), 288 pages, Talence, France, Feb. 3, 1995.

* cited by examiner

METHOD FOR DETECTING ANOMALIES IN A WATER DISTRIBUTION SYSTEM

CROSS-REFERENCE TO RELATED APPLICATIONS

This application is a National Stage of International patent application PCT/EP2016/065212, filed on Jun. 29, 2016, which claims priority to foreign European patent application No. EP 15306029.8, filed on Jun. 29, 2015, the disclosures of which are incorporated by reference in their entirety.

FIELD OF THE INVENTION

The present invention relates to the detection of anomalies in a water distribution system. More specifically, it relates to the detection of anomalies with the combined use of statistics and a hydraulic model of the water distribution system.

BACKGROUND PRIOR ART

A system for distributing drinkable water is notably made of pipes between a water head and consumers, along with control devices such as valves and pumps. Such system can be subject to numerous anomalies. Anomalies belong to a plurality of types. Hydraulic anomalies comprise leaks, abnormal variation of pressure, fast drop of the water level of a reservoir, incoherent mass balance of storage. Operation anomalies define an element in the system which is in an incorrect state, for example a valve in a opening state different to that stored in the information system. These anomalies, especially leaks, can dramatically reduce the performance of the water distribution system. For example, leaks in the pipes are the cause of the loss of a significant part of the water between water head and consumers, and can make structural damages. The detection and correction of anomalies in a water distribution system is therefore a permanent concern of the operators of such systems in order to mitigate the economic cost of water loss and damages. Moreover, the detection of leaks in a water distribution system is a key objective for limiting the global water consumption and waste, which is of particular interest in regions subject to water stress, and in view of promoting sustainable development.

The detection of leaks in a water distribution system is historically performed through human inspection. Human inspection generally consists in sending human operators to inspect pipes of the system and identify leaks and other anomalies. This detection can for example be aided using audio sensors, which detect noise due to a leak. However, the typically large size of water distribution systems renders human detection of leaks and anomalies very difficult. For example, the water distribution system of a large city comprises thousands of km of pipes. It is therefore impossible to inspect all pipes frequently at a reasonable cost.

The use of sensors contributes to a solution to the issue of detecting anomalies in a water distribution system. Sensors can notably be used for automatically detecting abnormal changes in the behavior of the system, therefore human operators can be sent to those nodes/arcs of the system wherein abnormal behavior was detected. However, sensor-based detection methods of anomalies have disadvantages as well. They can generate a high number of false positive (alarms for events which are not actual anomalies), and lead to numerous useless and costly human interventions. They can also properly detect anomalies but with imprecise localization, due to the large scale of a typical water distribution system. Otherwise, deploy a high density of sensors in the system could help in locating anomalies more precisely, but it is too costly.

The U.S. Pat. No. 8,635,051 discloses a method for identifying leaks in a water distribution system. This method comprises using a model of the leaks, and iteratively applying this model in order to obtain predicted values of water consumption, comparing the output values to observations, updating the values in order to obtain a better model, until the difference between predictions and observations is below a threshold, or a limit of the number of iterations is reached. The use of an hydraulic model by this method permits to identify a leak in a node wherein no sensor is available. However, it lacks an historical comparison for comparing observations to historical data. Thus, the robustness of the prediction is lowered, since a threshold for detecting a leak or abnormal value needs to be defined a priori.

There is therefore a need for a method for improving the robustness of automatic detection and localization of anomalies in a water distribution system. The proposed method is based on the use of a hydraulic model, and a statistical processing of time series of measurements at selected nodes of the system.

SUMMARY OF THE INVENTION

To this effect, the invention discloses a method for detecting anomalies according to claim 1, a system for detecting anomalies according to claim 14 and computer program product according to claim 15. Dependent claims define preferred embodiments of the present invention.

The invention also discloses a method for detecting anomalies in a water distribution system composed of a network of nodes, said method comprising: A) parametrizing a hydraulic model of the water distribution system by initializing a set of values of control variables characterizing the network and its output at the nodes; B) using sensors on the network to acquire observations of a subset of the state variables, said observations having time references; C) changing the set of values of the control variables; D) using the hydraulic model to calculate predicted values of a set of state variables characterizing at least water velocity and pressure at the nodes at the time references; E) computing residue values of the set of state variables as a difference between predicted values and observations at the time references; F) if said differences satisfy a break criterion, going to step H); G) if not, changing the set of values of the control variables and going back to step D); H) if said differences satisfy a refinement criterion, going to step J); I) if not, selecting an subset of the network where to calculate predicted values, going back to step D); J) classifying an entity of the network in a state according to the set of control variables.

Advantageously, steps C) to J) are performed for at least one event type, and changing the state of control variables is performed according to said at least one event type.

This permits to modify control variables that are known to be affected by an event, thus increasing the reliability and robustness of event detection.

Advantageously, a plurality of event types is tested, and one instance of steps C) to J) is performed for each event type.

This permits to detect in a single execution of the method a plurality of types of events or anomalies on the network.

Advantageously, the refinement criterion comprises the calculation of values of one of a least square and a Bayesian objective function, and the selection and modification of control variables is determined by a Levenberg-Marquardt algorithm.

Using a Bayesian objective function permits to calibrate the relative confidence of the measurements and modified values of control and state variables. Using Levenberg-Marquadt algorithm permits to have good convergence and stability qualities.

Advantageously, classifying an entity of the network is performed by a previously trained machine learning algorithm.

This permits to have rules of classification optimized for a given water distribution system, whose reliability increases over time.

Advantageously, the control variables comprise scalar variables characterizing the topology and the topography of the network, and time-based variables characterizing the inputs and outputs of the network having at least one value at each time reference.

This permits to increase the number of possible events detected by the method.

Advantageously, changing the set of values of the control variables comprises modifying at least one of: the values of a subset of the time-based control; the values of a subset of the scalar control variables calculated during a phase of modeling of the network.

This permits to take full advantage of the availability of scalar and time-based control variables.

Advantageously, modifying the values of a subset of the time-based control variables comprises modifying the values of the time-based control variables representative of water consumption.

This permits to detect events which are detected by an abnormal increase of water consumption, for example leaks.

Advantageously, state variables further characterize pressure.

This permits to have a more complete and efficient modeling of the temporal evolution of the physical parameters of the water distribution system.

The invention also discloses a method of detecting anomalies in a water distribution system composed of a network of nodes, said method comprising: parametrizing a hydraulic model of the water distribution system with a set of values of control variables characterizing the network and its output at the nodes; using sensors on the network to acquire observations of a subset of the state variables at time references; using the hydraulic model to calculate predicted values of a set of state variables characterizing at least a water velocity at the nodes, said values having time references; computing residue values of the subset of the state variables as a difference between predicted values and observations at the time references; performing a statistical analysis of residue values at an entity of the network at a selection of the time references; classifying the at least one of a node and an arc of the network based on a quality index at the output of the statistical analysis.

Advantageously, the statistical analysis comprises the calculation of one of a mean, a standard deviation, an absolute mean or median deviation, an auto-regressive model, boxplot, Support Vector Machine, a Principal Component Analysis (PCA), K-nearest neighbor and results of statistical tests (computing P-values).

This permits a better understanding of the historical behavior of the water distribution system, and an adaptation of the detection to new situation with the feedback of users.

Advantageously, a node is classified in a class representative of an abnormal state if the residue values at the entity of the network exceeds a threshold based on statistical analysis of historical data and operational risk level a predefined number of successive time references.

Advantageously, a method comprising the step of the two methods described above further comprises classifying the network in a state at the output of: J) Classifying an entity of the network in a state according to the set of control variables, and; classifying the at least one of a node and an arc of the network based on a quality index at the output of the statistical analysis.

The invention also discloses a system for detecting anomalies in a water distribution system composed of a network of nodes, said system comprising: sensors of at least water velocity and pressure at a subset of nodes of the network; a computing device comprising a processor; communication links between sensors and the computing device; a storage media; wherein the computing device is configured for: retrieving an initial set of values of control variables characterizing the network and its output at the nodes from the storage media and using it to parametrize a hydraulic model of the water distribution system; using communication links between sensors on the network to acquire observations of a subset of the state variables, said observations having time references; executing one of the method disclosed above.

The invention also discloses a computer program product, stored on a non-transitory computer-readable medium, detecting anomalies in a water distribution system composed of a network of nodes, said computer program product comprising code instructions for executing one of the methods disclosed above.

The invention improves the reliability of detection and identification of abnormal states in a water distribution network.

The invention is applicable to a wide range of anomalies, comprising detection of leaks, degradation of water quality, issue with sensor, and incorrect behavior of device of the drinking water distribution system.

Anomalies detected by the method and confirmed by operators can be used to feed learning algorithms in order to detect further anomalies with an increased accuracy.

The method has an improved robustness thanks to the use of historical measurements. The method takes into account the observed variability and uncertainty of the measurements.

The method eases localization and identification of anomalies, and is able to present anomalies to an operator sorted by criticality.

The method reduces the cost of operating a water distribution system, by limiting the number of human interventions on the system.

The method reduces the cost of operating a water distribution system, by limiting the number of sensors required for precisely locating anomalies.

All embodiments described in the present specification may be combined in any combination, except mutually exclusive combinations.

BRIEF DESCRIPTION OF THE DRAWINGS

The invention will be better understood and its various characteristics and advantages will emerge from the following description of a number of exemplary embodiments and its appended figures in which.

DETAILED DESCRIPTION OF THE INVENTION

In this specification, the invention will be described by way of examples related to the detection of a valve in a false opening state, an issue with sensor, and a leakage event. However, the invention is not restricted to these examples and can be applied to the detection of any anomaly in a water distribution system.

Figure 1:
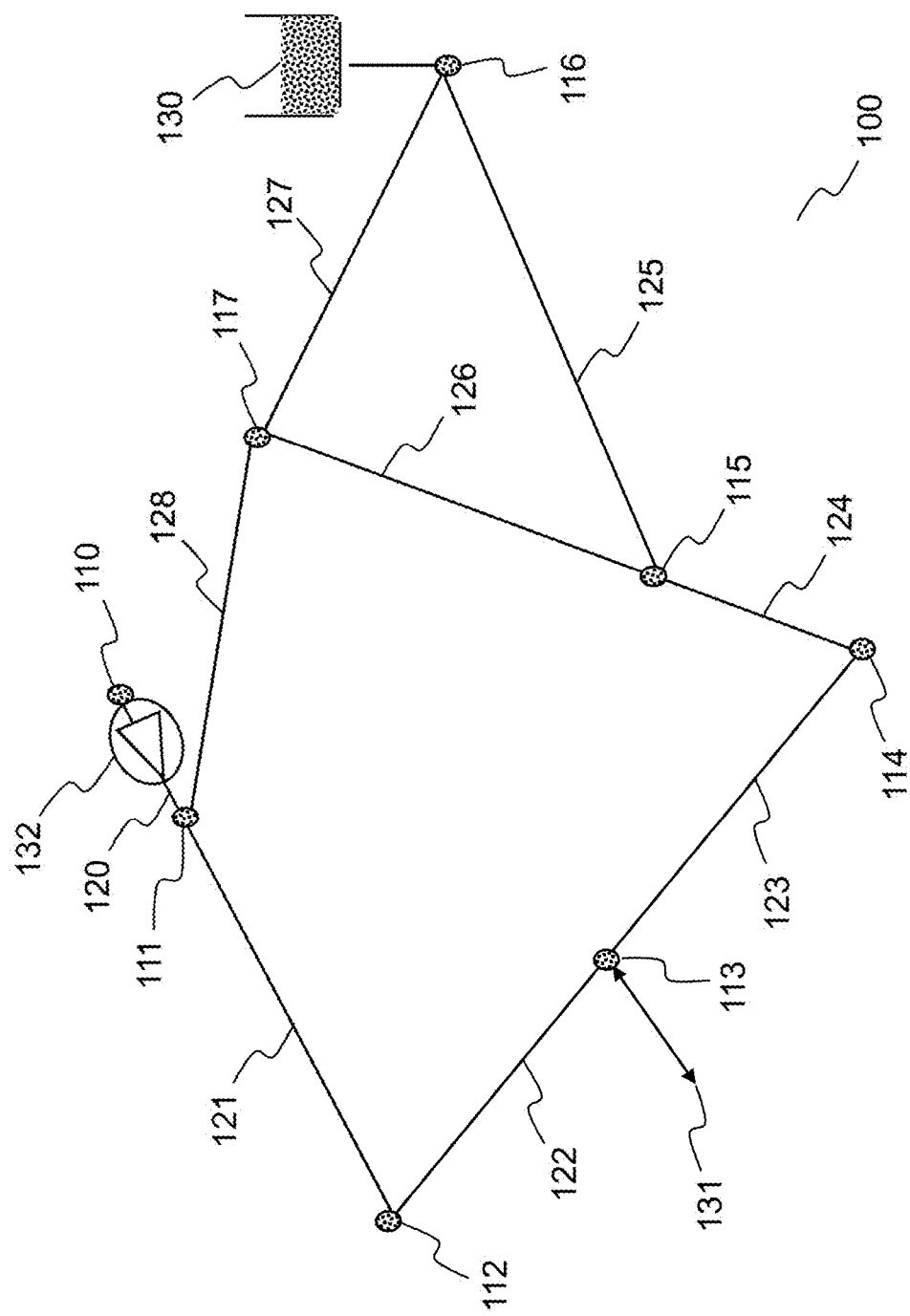
FIG. 1 displays an example of a water distribution system organized in network in prior art.

FIG. 1 displays an example of a water distribution system organized in a network according to the prior art.

The network 100 displayed on FIG. 1 is organized as a network and comprises a plurality of nodes 110, 111, 112, 113, 114, 115, 116 and 117, and a plurality of arcs 120, 121, 122, 123, 124, 125, 126, 127 and 128. The nodes typically represent the connections with water sources or water reservoirs, for example the reservoir 130 at node 116, the connections with the user of the water distribution system, for example consumption 131 at node 113 and the connections between the arcs. The arcs typically represent pipes between the nodes. The network can be equipped with equipments such as valves and pumps. A pump 132 is for example present on the arc 120. More generally, a node can be a junction between two or three pipes, a point at which inputs or outputs of the network are found, for example a point where a user consumes water, or a point at which water is injected in the network. A node can also represent a sub-network, for example a neighborhood grouped under a single node.

Physical parameters related to water notably comprise by way of example velocity, pressure, flow rate, level in storage (reservoir and tank), temperature, etc. . . . . Further parameters can be added according to detection needs and/or the evolution of sensors. The evolution of these parameters over time depends on the characteristics of the water distribution system, the inputs and outputs at the nodes, and the state of the any equipment in the system.

The attributes of the water distribution system notably comprise:
the topology of the network (i.e. the graph with arcs and nodes);
the topography of the network (i.e. the elevation of the nodes, the properties of the pipes such as length, diameter, material, roughness, singularities, minor loss coefficients . . . );
the properties of each equipment of the network (for example pump characteristics, valve diameter, friction coefficient, operating setpoint, . . . ). The hydraulic model of a drinking water network comprises this set of information.

The inputs and outputs at the nodes are defined by the consumptions or injections of water at every node of the graph. They typically represent the individual consumptions of the users of the water distribution system, and the injection of water from water inlet into the system.

The status of equipment, such as valves or pumps, comprises the operating states and setpoints of device.

In the remaining of this description, the characteristics of the water distribution system, inputs and outputs at the nodes and states of the devices will be referred to as "control variables" of the water distribution system, while the physical parameters at the nodes and arcs will be referred to as "state variables" of the water distribution system. The values of state variables vary with time. The values of some control variables, for example those related to the topology or the topography of the network, remain constant, while the values of some control variables, for example those related to the inputs and outputs of the network and to the states of devices, vary over time. Meanwhile, an entity refers to the whole network, or a subset of a network composed of nodes, arcs and equipments, a single node, a single arc or an equipment of the network which is characterized by characteristics that have an impact on the behavior of the water distribution system.

A description of the initial value of state variables and a prediction (time series) of the values of the control variables, notably the consumptions at nodes of the network, permit to predict the values of state variables over time. This prediction is generally performed by computing successive values of the state variables with fixed or variable time step. This prediction is called resolution of the direct problem.

Some entities of the network are equipped with sensors measuring physical parameters, typically velocity or pressure. These sensors permit to obtain time series of state variables.

Methods are known for computing the values of control variables that define the goodness-of-fit of the system beside the observations of state variables. These methods are generally called inverse problem solving and are notably disclosed by Piller, O. (1995): Modeling the behavior of a network—Hydraulic analysis and sampling procedures for parameter estimation. Applied Mathematics thesis from the University of Bordeaux (PRES), 288 pages, Talence, France, defended on the 3 Feb. 1995 and Piller, O., Gilbert, D. and Van Zyl, J. E. (2010): Dual Calibration for Coupled Flow and Transport Models of Water Distribution Systems. Water Distribution Systems Analysis WDSA 2010, ASCE, Tucson, 722-731, December 2010, U.S. Pat. No. 8,635,051. Solving an inverse problem generally consists in successive iterations of a loop comprising modifying values of control variables, predicting values of state variables according to control variables, in order to minimize a mathematical function that is representative of the differences between prediction and observations of state variables. These techniques permits to determine for example the characteristics of an entity of the network (e.g. a loss of charge in a node, a roughness of a pipe . . . ) or water consumption that best match the observations of state variables.

Figure 2:
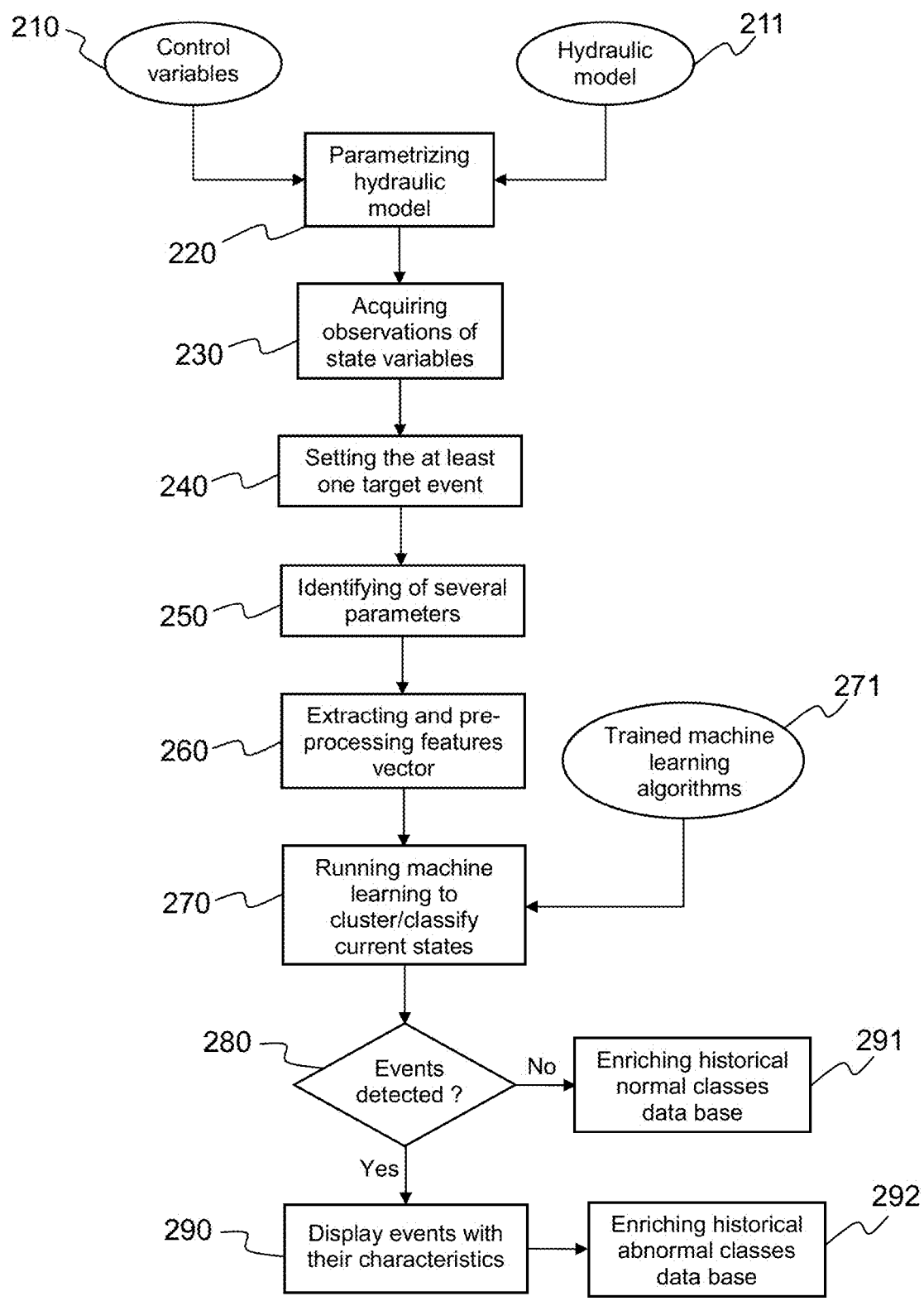
FIG. 2 displays an example of method for detecting anomalies in a water distribution system in a number of embodiments of the invention, using a stepwise iterative adjustment of properties and control variables of a hydraulic model combined to a machine learning for identifying the anomaly.

FIG. 2 displays an example of method for detecting anomalies in a water distribution system in a number of embodiments of the invention, using a stepwise iterative adjustment of properties and control variables of a hydraulic model and machine learning for identifying the anomaly.

The method 200 comprises a first step 220 for defining parameters of a hydraulic model 211 using a set of control variables 210. The nature of the hydraulic model and control variables has been presented in relation to FIG. 1. The hydraulic model can notably be configured with control variables characterizing the structure of the network and control variables characterizing a prediction of the inputs and outputs of the network at nodes over a set of time references, notably a prediction of water consumption in the network.

In a preferred embodiment, the values of the control variables related to the structure of the network (e.g. the diameter and roughness of the pipes, characteristics of equipments, etc. . . . ) have been calibrated after the creation of the hydraulic model. Indeed, theoretical values defined during the modeling of the network do not always match real values. In order to obtain more accurate values of control variables related to the structure of the network, a calibration step may consist in adjusting the values of these control variables in order to provide the best prediction of the behavior of the network. Typically, this adjustment may consist in:
- performing observations of the inputs, outputs and a subset of the state variables of the network for a certain duration;
- configuring the hydraulic model of the network with values of the control variables related to the inputs, outputs and structure of the network;
- calculating predicted values of the state variables of the network according to the hydraulic model;
- calculating a difference between observed and predicted values of the state variables of the network, and modifying the values of the control variables of the network using an optimization algorithm in order to minimize the distance between observed and predicted values of the state variables of the network.

On the other hand, control variables related to the input and output of the network can be obtained for example using observations of the past inputs and outputs. For example, the values of control variables characterizing water consumption at different nodes can be calculated using historical metered data of water consumption.

The method 200 further comprises a step 230 of using sensors to acquire observations of a subset of state variables, said observations having time references. As stated in relation to FIG. 1, a water distribution system is typically equipped with sensors. These sensors measure physical parameters such as velocity, flow rate, pressure, etc. at the nodes or the arcs of the network, said physical parameters at a node or an arc being state variables of the network. For practical reasons of cost, maintenance and easiness of operation, all nodes and arcs are not equipped with sensors, and those equipped with sensors are usually not equipped with a sensor for each physical parameter. The number and distribution of sensors can be chosen in accordance with the definition of sectors of the water distribution system. The acquisition of observations can be performed remotely. For example, the sensors which are deployed along the network can send the values of state variables to a remote platform through various telecom means, usually wireless links.

The values of state variables vary over time, each value has a time reference that represents the time at which the value has been measured. In an embodiment of the invention, values of state variables are acquired using a predefined time period and sent regularly using another period. For example, values of the state variables for which a sensor is present can be acquired and sent every two minutes, 5 minutes, 15 minutes or every hour each 24 hours. In a preferred embodiment of the invention, sensors are synchronized in order to acquire measurement simultaneously. This allows the remote platform to acquire observations of the values of the subset of state variables for which a sensor is available at each time reference. Values can be sent immediately after being measured. They can also be stored locally at transmission device level, and then sent at regular intervals, for example by sending all values that have been captured during 15 minutes, 1 h or any other interval.

The method 200 further comprises a step 240 of setting the at least one target. The step aims at defining targeted events which can be for instance an abnormal variation of pressure, the detection of a valve in a false opening state. These targeted events will be then those to be sought in the following steps of the method, for various entities (whole network, subset of the network . . . ). As explained with reference to FIG. 3, a set of parameters is defined per each type targeted event in the step 310.

The method 200 further comprises a step 250 of identification of parameters. In a number of embodiments of the invention, the parameters are set for targeted events. In cases wherein a plurality of events are targeted, a step 250 of identifying is executed for each target event, either one after the other, or in parallel. An example of method for identifying parameters in one instance is provided below, with reference to FIG. 3. Various methods exist for determining target events. In a number of embodiments of the invention, events are picked in a predefined list. In other embodiments one event is selected for a specific application. For example, only a "leak" event may be selected. In yet other embodiments of the invention an operator selects the events it is interested in a list of all possible events. In yet other embodiments of the invention, events that are detectable according to the sensors present in the network are selected. In other embodiments of the invention, no particular event is searched. Thus, a predefined set of parameters can be selected.

Figure 3:
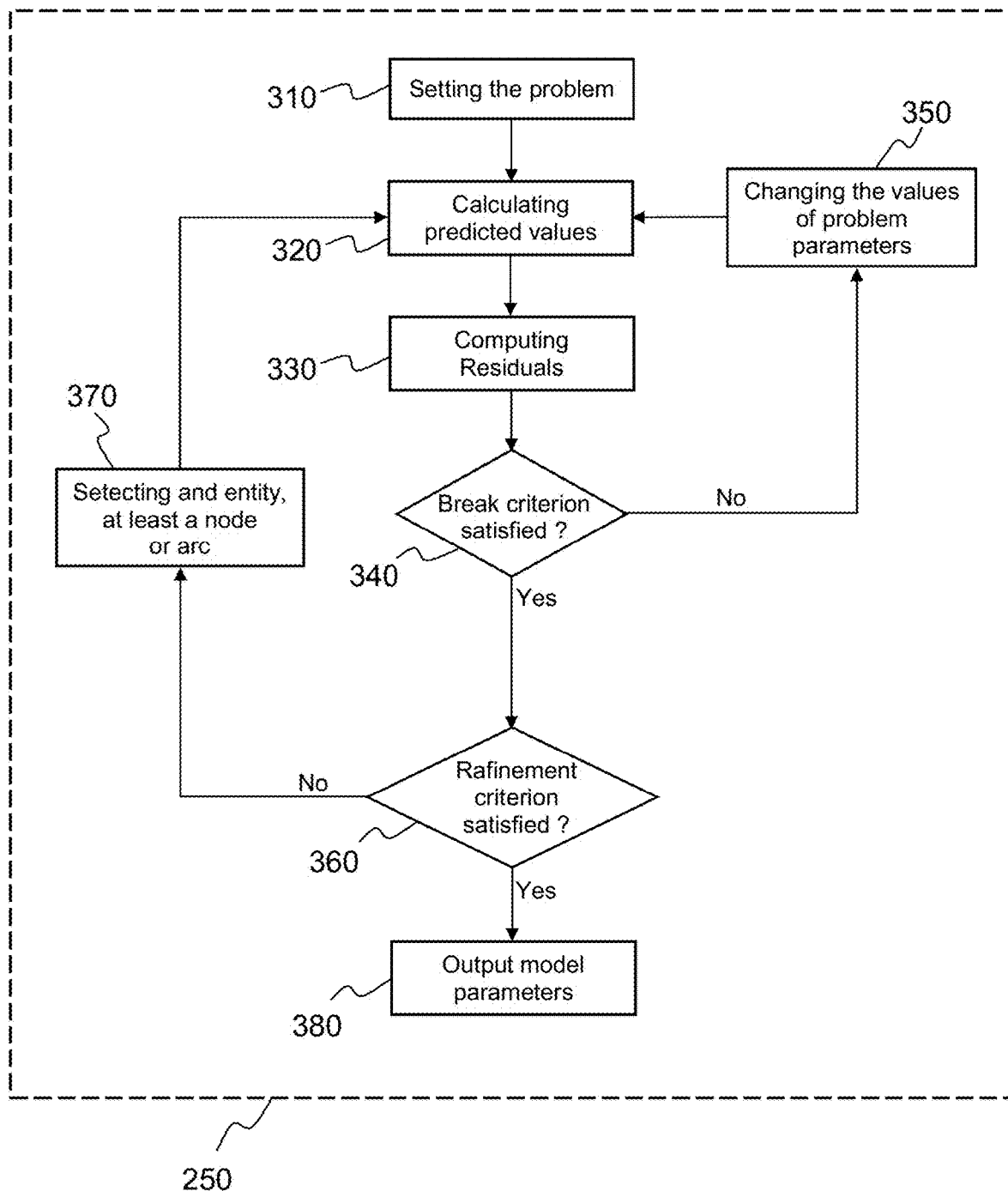
FIG. 3 displays an example of a method for identifying parameters for a target event in a number of embodiments of the invention.

The method comprises a step 260 for extracting and preprocessing features vector to prepare the classification step. The process aims at normalizing data and reducing the dimension of the problem. The input data include all model outputs (Cf. FIG. 3) and the output data is a vector with a reduced number of dimensions. In an embodiment the problem dimension reduction can be solved using either a Principal Component Analysis, Linear Discriminant Analysis or K-nearest neighbor algorithm.

The method comprises a step 270 to qualify the current state of an entity. In accordance to the definition of an entity proposed earlier, the classification of an entity may apply to the whole network, a single arc, a single node or a subset of the nodes and arcs of the network. In a number of embodiments of the invention, the subset of nodes and arcs of the network that form the entity are chosen so as to form a coherent set. For example, an entity may be a subset of an area that delivers water to a neighborhood, with a single input and a single output arc for the whole entity.

Various machine learning techniques can be used depending on the availability and amount of historical labeled data, composed of features vectors. In a number of embodiments, these techniques include outlier detection, clustering and classification. In a number of embodiments, the rules of machine learning are based on machine learning algorithms 271 previously trained on historical labeled features vectors. For example in the case of sufficiently available historical labeled classes, classification algorithms can analyze available historical classes and corresponding features vectors in order to build a classifier to automatically determine rules of classification of entities. A new vector of features can then be automatically classify into the relevant current class, therefore characterizing the current state and giving a valuable information to operator. For example the classification may be based on Support Vector Machine, Random Forest; Logistic Regression . . . . In a number of embodiments, classification with two classes (normal/abnormal state) can be used. In a number of embodiments classifications may also consist in types of anomalies (pressure, high/low consumption, and water quality), etc. The classification can also include an index of confidence, which indicates the certainty of the classification of the anomaly. In a number of embodiments, training of the machine learning algorithm can be triggered at any time depending on time basis (defined frequency), on performance criteria or on evolution in the used data set.

In the case of not sufficiently available labeled historical classes and corresponding features vectors, clustering or outlier detection can be used. Clustering may include techniques such as K-means or hierarchical clustering. Clustering uses past states, represented by past features vectors but without known labels. In one embodiment of the invention, the state is then declared as abnormal if not present in bigger clusters (a criterion of the size of clusters is tested).

The method comprises a step 280 to determine whether the class computed for an entity corresponds to an abnormal state ("event") according to the output of machine learning algorithms or if one of the states is detected as outlier. If an event is detected, the method goes to 290. If the states are qualified as normal, the method goes to 291.

The method comprises a step 290 to display structured information to the operator. A list of prioritized entities in abnormal state can then be presented to an operator in order to launch proper maintenance operations to the entities with the highest likeliness of anomaly. These entities with abnormal state are presented with additional information collected all along the previous steps (based on information contained in the model outputs and the features vector). In one embodiment, the information contains indications about quantification of the level of abnormality (for instance the value of flow of a leak, the value of head loss), time and duration of the abnormality, known location and spread of the abnormality etc. Taking into account the context settings, this information is used to prioritize the abnormal states and provide a degree of abnormality to the user.

The method comprises a step 291 to enrich historical data base of vectors of features labeled as "normal". These vectors of features are used as inputs for the learning process of algorithms. This advantageously permits to have a richer database over time, and thus a more reliable prediction of normal or abnormal states.

The method comprises a step 292 to enrich historical data base of vectors of features not labeled as "normal" by the method. The method comprises then a step of validation of events by the operators. In one embodiment, the operators can then input in the method, for each entity, if they confirm the event and its class. The vectors can then be labeled according to the class they belong (leak, pressure anomaly, water quality anomaly . . . ). The historical data base of vectors of features is enriched with the new classified vector of features whatever the state is "abnormal" or "normal".

These vectors of features are used as inputs in the learning process of algorithms. In case not labeled by the operator, the vectors are still stored but without specific label. They can then be used in unsupervised or semi-supervised modes (clustering and outliers detection).

The FIG. 3 displays an example of a method for identifying parameters for a target event in a number of embodiments of the invention.

The method 300 comprises a step 310 of setting the problem according to one of the targeted events and specific entities chosen in step 240. The step aims at defining the sets of parameters corresponding to the type of targeted event for the entity. A set of parameters is defined per each target of event and entity. In a number of embodiments of the invention an event type is associated with a list of parameters, and the set of parameters is retrieved according to the event that is targeted. For example a false opening state of a valve is known to be characterized by inconsistent values of control variables representative of roughness and friction, while leaks are known to be characterized by abnormal values of water demand.

The method 300 further comprises a step 320 of using the hydraulic model to calculate predicted values of a set of state variables characterizing entities, at least velocity at the arcs and pressure at the nodes at the time references. This step consists in calculating a predicted value of state variables of the entity (network, its subsets, . . . ), at the time references of the observations. Methods for using a hydraulic model to calculate predicted values of the state variables of a hydraulic network are well known by people skilled in the art of water system engineering. They typically consist in, starting from the tank state at a time reference and the values of control variables, using the physical law of hydraulics for computing values of all state variables at the same time reference, and then computing values of the tank state at the next time reference. It is then possible to calculate predicted values of the state variables at all time references starting from initial values of the state variables and values of the control variables. Methods for calculating predicted values of state variables at a time reference are notably disclosed by O. Piller, "Modeling the behavior of a network—Hydraulic analysis and sampling procedures for parameter estimation". PhD thesis in Applied Mathematics from the Mathematics and Computer Science Doctoral School at the University of Bordeaux (PRES), 1995, 288 pages, Talence, France.

The method further comprises a step 330 of computing residue values of the subset of the state variables as a difference between predictions and observations at the time references. This step consists in computing differences between predicted and pre processed (smoothing, data imputation, etc. to clean the signal) observed values of the state variables, for state variables for which observations are available. In cases where the system is correctly modeled and calibrated, and the inputs and outputs of the network are correctly defined, the observations and predictions of the state variables are very close: that meaning negligible residue values. Conversely, the residue values can be important that meaning an anomaly occurs like for example when a spatial consumption of water is wrong. The objective function is used to compute the importance of the residue values as a weighted norm.

The method 300 further comprises a step 340 of verifying if residue values satisfy a break criterion. This step consists in verifying if the residue values of state variables are small enough for considering that values of control variables accurately describe the behavior of the entity. The break criterion can be for instance a combination of threshold on number of iterations, threshold on the variation of residue values, threshold on the gradient of the objective function with respect to the set of parameters.

When the break criterion 340 is not satisfied, the method 300 comprises a loop step 350 to change the values of the problem parameters (for instance the consumption profile) using a descent method. In an embodiment the method can be gradient algorithm, conjugate gradient algorithm, Newton algorithm, Levenberg Marquardt algorithm . . . . This step 350 feeds a new iteration of the step 320, using hydraulic model to calculate predicted values with modified values of problem parameters.

When the break criterion 340 is satisfied, the method 300 comprises a step 360 which is a test based on a refinement criterion. While the value of the objective function decreases, further refinement step 370 is performed into the loop to step 320.

The method 300 further comprises a step 370 to select a subset of at least an element (node or arc). The step examines the gradient computed as the scalar product of element (node or arc) sensitivity vector by element contribution vector. The method discards the elements according to a selection criterion, based on sensitivity assessment. In an embodiment, those having a positive sensitivity are discarded. This step 370 feeds a new iteration of the step 320, using hydraulic model to calculate predicted values on the selected elements.

The method 300 further comprises a step 380 to provide the outputs of the model parameters. The model outputs include the adjusted parameters, the successive values of the element sets and related objective function, and characteristics which are processed into the step 260 as shown in FIG. 2. The model outputs include therefore information on various entities, from specific node or arc to subset of the network and the whole network.

Example of Embodiment: Detection of a False Opening State of a Valve

By means of non-limitative example of the method 200, a scenario of detection of a false opening state of a valve will be described below.

A hydraulic model has been defined and calibrated during a calibration phase, using different opening states of valves. The opening states of valves may vary over time, and the control variables representing their position need to be updated accordingly. However it is not always the case, especially if valves are not equipped with sensors and if they are operated manually.

A number of different classes of anomalies have been defined, that comprise anomalies such as leaks and errors of updates of the state of devices, such a false opening state of the valves. Machine learning algorithms have been trained to obtain classifiers on historical labeled features vectors corresponding to each type of anomaly.

Several instances of a method of identification of anomalies are executed, each one operating on different model parameters. For example a false opening state of a valve is known to be characterized by inconsistent values of control variables representative of roughness and friction, while leaks are known to be characterized by abnormal values of demands. Both result in a combination of inconsistent values of pressure and flow.

Each execution of the method 250 therefore modifies its own set of problem parameters, and the presence of a corresponding anomaly at an entity (arc or node, or subset of the network) can result in an important modification of the corresponding parameters. Outputs from simulations are used in the features extraction algorithm and pre-processing algorithm to obtain features vectors for each entity. The features vectors are then used in the classifier to select the current class for each entity. For example, if the execution of the method 300 significantly modifies the values of roughness and friction at a subset of arcs, and this subset contains arcs equipped with a valve, the subset of arcs can be classified in a class representative of an incorrect position of the valve.

This information is presented to an operator, who can launch a human inspection in order to validate the incorrectness of the opening state of the valve and correct its opening state if necessary. Once the correctness of the classification has been established, it is possible to use this data to further train the classification method for valves being in a false opening state. Indeed, the efficiency of classification (number of false alarms, number of true detection . . . ) based on learning is known to increase with the number of classification cases.

Figure 4:
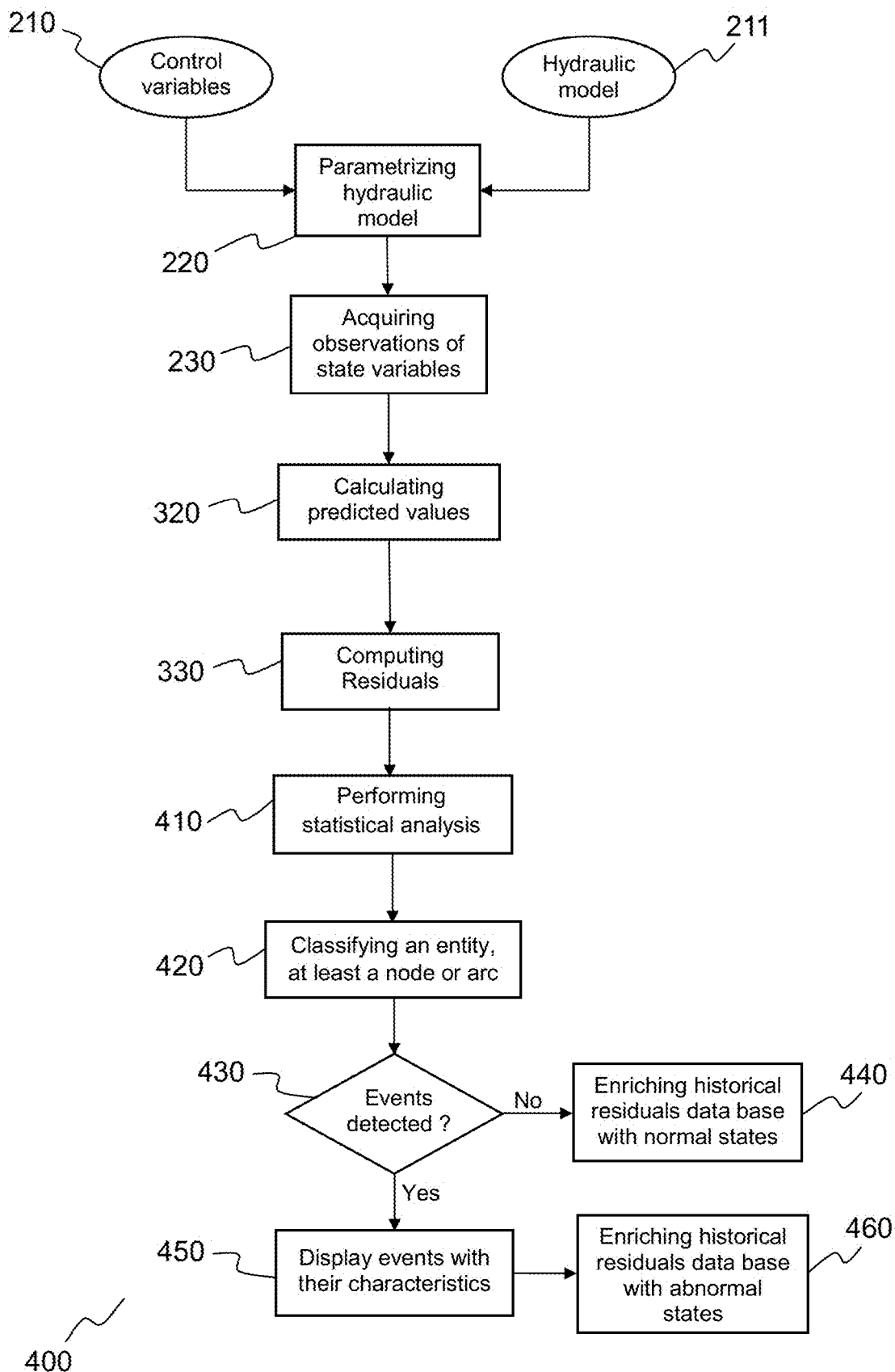
FIG. 4 displays an example of method for detecting anomalies in a water distribution system in a number of embodiments of the invention, using a statistical analysis of the residue values from comparison the result of hydraulic model and observation.

FIG. 4 displays an example of method for detecting anomalies in a water distribution system in a number of embodiments of the invention, using a statistical analysis on residue values from the hydraulic model.

The method 400 comprises:
- a step 220 of configuring a hydraulic model 211 of the water distribution system with a set of values of control variables 210 characterizing the network and its output at the nodes;
- a step 230 of using sensors on the network to acquire observations of a subset of the state variables at the time references;
- a step 320 of using the hydraulic model to calculate predicted values of a set of state variables characterizing at least a velocity at the nodes, said values having time references;
- a step 330 of computing residue values of the subset of the state variables as a difference between predicted values and observations at the time references;

These steps are similar to those of the method 200 and 300. In a preferred embodiment of the invention, residue values are calculated for all entities at which observations of the state variables are available.

The method 400 further comprises a step 410 of performing a plurality of statistical analyses of residue values for at least an entity for a selection of time references. This step consists in analyzing the distribution of residue values for an entity at each time reference in a time window. According to various embodiments of the invention, the time window may cover the totality or a subset of time references.

Through the plurality of statistical analyses, an anomaly can be set if residue values are not consistent with historical observations of residue values. The use of historical distribution of residue values enables to catch the usual and unusual behaviors, including variability and various properties of the residue values, to be compared with current residue values on given time window. For example the step 410 may comprise statistical inferences (n-order moment, average, standard deviation, mean or median absolute deviation, etc.) calculation using historical residue values data base to be compared with the corresponding statistical inferences from the current residue values. This gives more robustness to the method as it takes into account the past values.

In a number of embodiments of the invention the residue values are transformed using a Fourier transform prior to statistical analysis. In an embodiment of the invention, performing statistical analysis for an entity comprises detecting if the value of a residue value exceeds a predefined threshold for a predefined number of successive times. The threshold and number of successive times can be predefined according to previous detections, in order to maximize the ratio of detection of anomalies when an anomaly is present, and minimize the ratio of detection of an anomaly when it does not exist (false alarms). The analysis can be composed of statistical tests on properties of residue values, and the computation of resulting Pvalues to qualify the result of the tests. The thresholds on Pvalues can be set to obtain a level of risk of obtaining false alarms. Setting a given value then implies expecting a given percentage of false alarms, i.e. wrong reject of assumptions. In an embodiment, the statistical analysis is typically performed on residue values of pressure or velocity. For example an analysis of flow rate for detecting a leak may be performed on windows of a few hours.

The method further comprises a step 420 of classifying the at least an entity of the network based on rules to be applied to the output of the statistical analysis step. Following the application of the rules, a class is given to the entities (for instance "leak", "pressure drop", "water quality issue"). In an embodiment of the invention, the rule is based on a comparison of Pvalues given by statistical tests performed in step 410, with a predefined level of risk, depending on the target level of sensitivity of the method. In an embodiment of the invention, the rule is based on previously trained classification algorithm, enabling, based on past simulation, to analyze current vector of residue values and give the current class of the entity. In an embodiment of the invention, two classes are available, one representative of normal and the other representative of an abnormal states. In other embodiments of the invention, classes give a more accurate nature of anomaly, such as "abnormal drop of pressure", "problem with water quality" etc.

The method comprises a step 430 determining the following step according to the current classes. If one of the classes corresponds to an abnormal state (one of the possible abnormal states) or if the state is detected as outlying, the method goes to 450. If all the classes are qualified as normal, the method goes to 440.

The method comprises a step 440 to enrich historical data base of residue values with residue values of entities labeled as "normal" on the current time window. These residue values are used in the statistical analyzing process to provide information on usual distribution of residue values.

The method 400 comprises a step 450 for displaying the events with their characteristics. Anomalies can then be presented to an operator, for example in a sorted list, or on a graphical interface. In a number of embodiments of the invention, the method further comprises a step of quantifying the criticality of an anomaly. This step can for example consist in ranking the anomalies from the most to the least severe. This ranking may be performed for example according to the importance of the residue values, the time during which significant residue values are found or the nature of the physical parameter on which high residue values apply. The quantification of a leak may for example be calculated according to the estimated volume of the leak. In an embodiment of the invention, only the anomaly considered as the most severe is presented to the operator. The operator then can send human inspection to verify the nature of the anomaly, and fix it if necessary. It has also the ability to assert the correctness of the detection of the anomaly (user labeling), in order to provide additional training cases and improve the future detection of anomalies.

The method comprises a step 460 to enrich historical data base of residue values with residue values of entities not labeled as "normal" on the current time window. These residue values are used in the statistical analyzing process to provide information on unusual residue values distribution.

Example of Embodiment: Detection of a Sensor Fault

By means of non limitative example of the method 400, a scenario of detection of a sensor fault will be described below.

A water distribution system equipped with water flow and pressure sensors has been modeled. The hydraulic relations between pipes, nodes and devices representative of the hydraulic model of network are described in modeling software files, for example Epanet (.inp/.net), Piccolo (.dat), Infoworks (.iwc) or Porteau (.xpto) files. The model has been calibrated in a prior calibration phase during which parameters or control variables representative of the structure of the network (for examples sizes of infrastructure, roughness, losses of charge) have been determined. The calibration of the model can be performed using temporary sensors in addition to permanent sensors, in order to have a more precise determination of the control variables than if only permanent sensors were used.

During a learning phase, the method is used with predictions of consumption, which can be adapted for example according to the date in the year and historical data of the measurements. Residue values are obtained by performing the difference between predicted and measured values. The residue values are stored, for all entities equipped with sensors. A detecting module can then be applied to the residue values, in order to establish if residue values are representative of a standard behavior of the system, learned on historical datasets of residue values. For example, values representative of the behavior of each node may be learnt. The model may notably comprise standard deviations of residue values, or parameters of auto-correlation of the series of residue values taking into account various operating contexts. Operating context may comprise every element that has an impact on the behavior of the network, e.g. the day and time, the current month or season, etc. . . . . The learning module can also determine, using the analysis of historical values, a limit value of a characteristic of the residue values, in order to adapt the sensitivity of the system. In the case of statistical tests for example, the threshold for Pvalues for rejecting assumption may be tuned to provide to the operator an acceptable number of expected false alarms. The level of risk of having false alarms is then dependent to the thresholds set. In the case of comparison of values with a linear combination of mean and a number of standard deviations (confidence envelope), the number of standard deviations can be set according to statistical process control principles. The expected number of false alarms can then be set. The characteristics of residue values are recorded.

In an operating phase, the method is applied to measurements of the sensors on a time window, for example 6 hours. Predicted values are calculated separately, using an initial state of the system and predictions of water consumption. Residue values are for example stored in a matrix, with one row per sensor and one column per time reference. Detection process can raise an abnormal sensor behavior, for instance a drift, a number of out-of-range values etc. This anomaly can be observed on predicted values by inconsistent values in certain measurement points. The anomaly is detected for example if the residue values are too high for a large number of successive values, or if their distribution, represented by an auto-regressive model, is different from historical distributions. The thresholds for detecting an anomaly have been determined in the learning phase using historical values. This embodiment is advantageous, since the use and comparison with historical values permits the detection of anomalies while limiting the number of false alarms.

The intensity of the anomaly can be calculated, on the ground of residue values, representative of the difference between observations and predictions. This intensity permits the qualification of the anomaly reported to the operator, with an indication of its seriousness. The measure of intensity helps the operator to compare the anomaly with previous ones on the same network, and decide the actions to be performed for solving the anomaly. In the case of sensor issue, maintenance can be comprised of physical action directly on sensor for instance.

Figure 5:
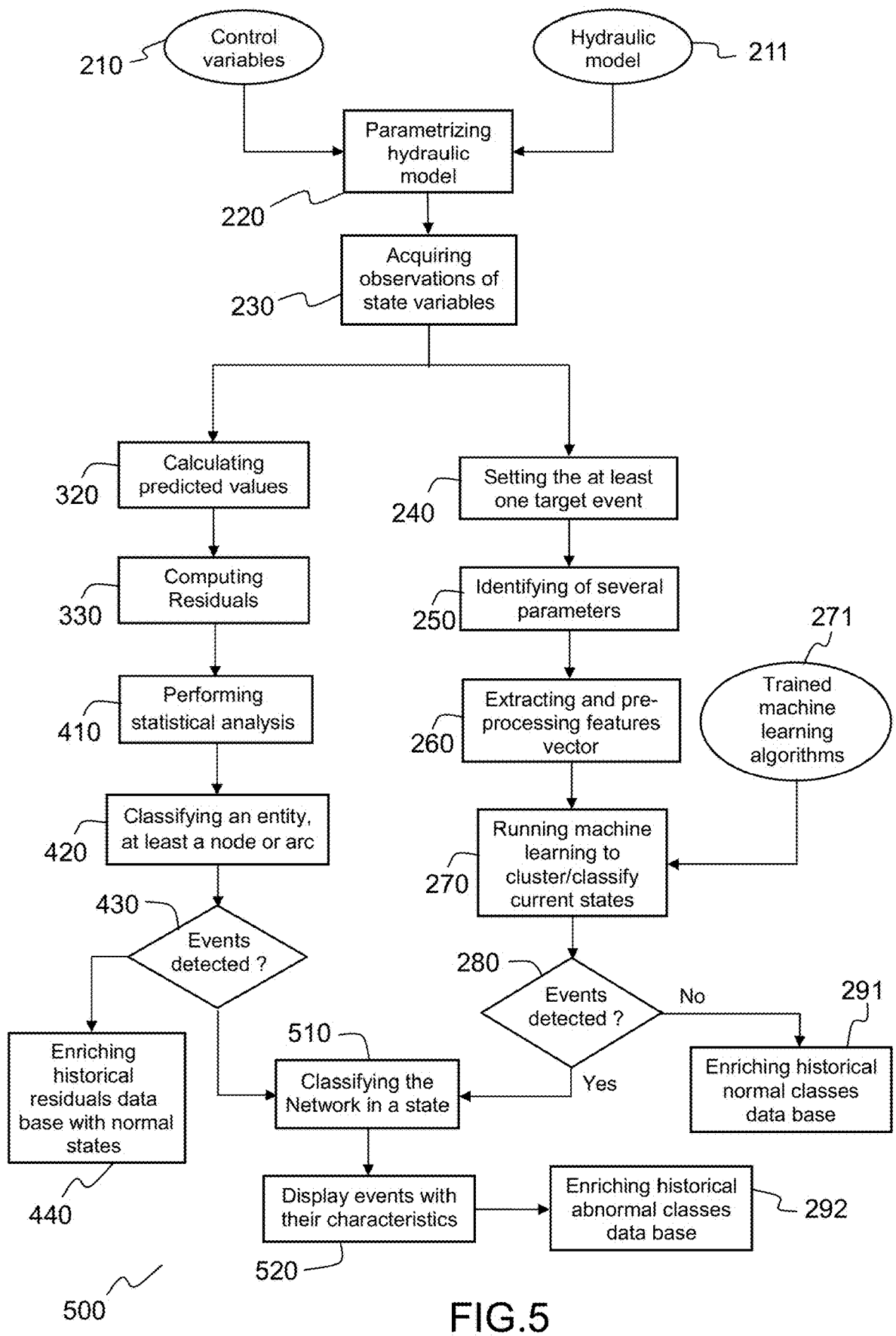
FIG. 5 displays an example of method for detecting anomalies in a water distribution system in a number of embodiments of the invention, using a combination of statistical analysis on residue values from the hydraulic, model for characterizing the calibration status and a stepwise iterative adjustment of properties and control variables of a hydraulic model, machine learning for identifying the anomaly.

FIG. 5 displays an example of method for detecting anomalies in a water distribution system in a number of embodiments of the invention, using a combination of statistical analysis on residue values from the hydraulic model for characterizing the calibration status and a stepwise iterative adjustment of properties and control variables of a hydraulic model, machine learning for identifying the anomaly.

The method 500 comprises:
- a step 220 of configuring a hydraulic model 211 of the water distribution system with a set of values of control variables 210 characterizing the network and its output at the nodes;
- a step 230 of using sensors on the network to acquire observations of a subset of the state variables at the time references;
- a step 240 of setting the at least one target, aiming at defining the sets of parameters corresponding to each type of targeted event.
- a step 250 of identification of parameters for each targeted event in a parallel process
- a step 260 for extracting and preprocessing features vector to prepare the classification step
- a step 270 to qualify the current states of entities with trained machine learning algorithms 271 depending on the availability of historical labeled data
- a criterion 280 determining the following step according to the current state for each entity
- if the criterion 280 is not satisfied, a step 291 to enrich historical data base with vectors of features labeled as "normal"
- if the criterion 280 is satisfied, a step 292 to enrich historical data base with vectors of features not labeled as "normal" by the method
- a step 320 of using the hydraulic model to calculate predicted values of a set of state variables characterizing at least a velocity at the nodes, said values having time references;
- a step 330 of computing residue values of the subset of the state variables as a difference between predicted values and observations at the time references;
- a step 410 of performing a statistical analysis of residue values at entities (at least a node) and at a selection of the time references;
- a step 420 of classifying the at least an entity of the network based on rules to be applied to the output of the statistical analysis step;
- a step 430 determining the following step according to the current classes;
- a step 440 to enrich historical residue values data base with residue values of entities labeled as "normal" on the current time window The steps 220, 230, 240, 250, 260, 270, 280, are similar to those of the method 200. The steps 320 and 330 are similar to those of the method 300. The steps 410, 420, 430, 440 are similar to the one of the method 400.

The method comprises a step 510 of classifying the network in a state at the output of steps 270 and 420. A number of different methods for combining the event detection using residue values and the event detection using the inverse hydraulic model into a global classification. In certain cases such detection is more precise and robust than a detection of event using only one of the branches. For example, in many cases event classification at step 420 is faster to train than event classification at step 270. Thus, at the beginning of event detection in a network, event classification at step 420 can provide a reliable detection of events after a lower number of training cycles than event classification at step 270. Meanwhile, the identification of parameters at step 250 permits to locate events more precisely, even in nodes that are not equipped with sensors. Indeed, modifying parameters at a node or arc, even not equipped with sensors, permits to locate an event at this node or arc. The combination of the both ways of detecting events thus advantageously combines the advantages of the both branches, and provides an event detection that is at the same time precise and fast to train.

A number of different ways are possible for detecting combining event detection. For example, it is possible to use machine learning algorithms on the events that are output of both steps 270 and 420, in order to train machine learning algorithms to raise an event in the most relevant cases of events raised by steps 270 and 420. In other embodiments of the invention, a more simple combination is used: when an event is detected in a node at step 270, the step 510 checks if the output of step 420 comprises an event in a neighboring node that is equipped with a sensor If yes, it checks if the two events belong to similar types. If it is the case, the event detected at step 270 is output by the system.

In other embodiments of the invention, events are not combined from events in the two branches, but an event classification algorithm is globally trained on the residue values at the output of step 330, and the feature vector at the output of step 260.

The method 500 comprises a step 520 which aims at displaying the output of the process 500 to the operator.

Example of Embodiment: Reduction of a Leak at an Early Stage of System Use

By means of non-limitative example of the method 500, a scenario of reduction of incorrect alarms when detecting a leak at an early stage of use of a system will be described below.

This example describes the detection of a leak after a few cycles of detecting and training using a method 500 according to the invention. The efficiency of machine learning algorithm is known to increase with the number of utilizations. It is a desirable property, since the reliability of the system of detection of events increase, and machine learning algorithms, when properly trained, can reach a very high level of reliability. However, in early stages of use of a system, insufficient training of machine learning algorithms may lead to incorrect alarms.

Machine learning based on matrices of residue values are generally trained faster than machine learning algorithms based on parameters at the output of an inverse hydraulic model, for at least because classification of matrices of residue values can be launched more often than the classification of control variables.

At an early stage of use of the system, a leak event is detected at step 270, although no leak is present. This false detection is due to an insufficient training of the machine learning algorithms. Meanwhile, the algorithm of classification based on residue values that had the ability to be trained in a lower number of cycles, did not detect any event. In this example, the step 510 discards the event, thus avoiding raising a false alarm.

Figure 6:
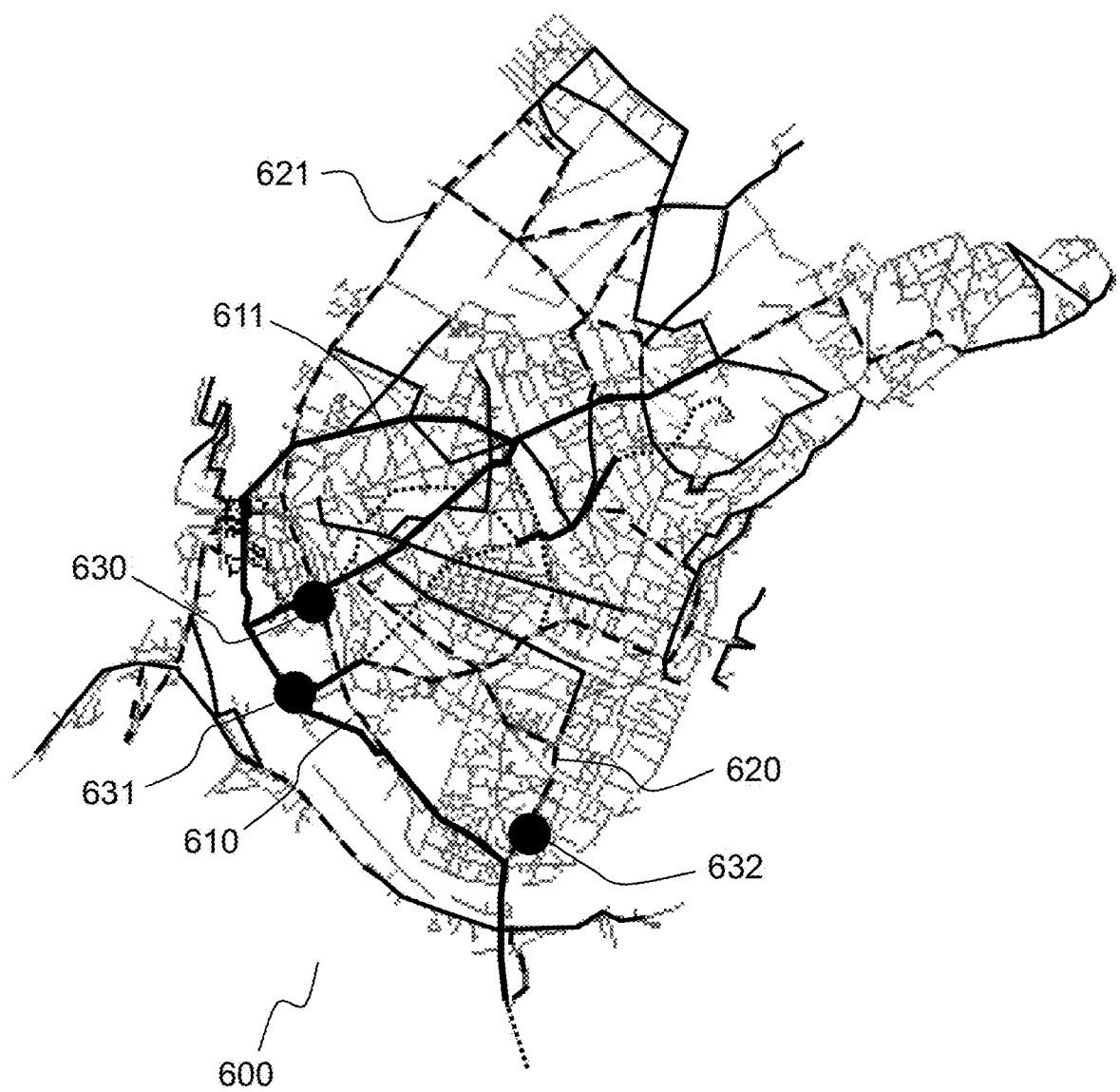
FIG. 6 displays an example of a presentation of the localization of anomalies to an operator.

FIG. 6 displays an example of a presentation of the localization of anomalies to an operator.

A map 600 of the network of a water distribution system is displayed to an operator through a display device. The map contains lines that represent pipes of the system, the width of the lines being representative of the diameter of the pipes. The system contains large pipes, such as pipes 610 and 611, and smaller pipes, such as pipes 620 and 621. Three leaks 630, 631, 632 have been localized in the network and are represented using large circles. Information about the relative importance of the leaks can be inserted. For example, the diameter of the circles may increase with the importance of the leak. It may also be possible to represent only the leak that is considered as the most severe, or display additional information about the leak, for example a list of past leaks that had the closest characteristics.

The examples described above are given as illustrations of embodiments of the invention. They do not in any way limit the scope of the invention which is defined by the following claims.

The invention claimed is:

1. A method for detecting anomalies in a water distribution system composed of a network of nodes, said method comprising:
   A) parametrizing a hydraulic model of the water distribution system by initializing a set of values of control variables comprising the network and its output at the nodes;
   B) using sensors on the network to acquire observations of a subset of state variables, said observations having time references;
   C) changing the set of values of the control variables;
   D) using the hydraulic model to calculate predicted values of a set of state variables comprising at least water velocity and pressure at the nodes at the time references;
   E) computing residue values of the set of state variables as a difference between predicted values and observations at the time references;
   F) if said differences satisfy a break criterion, going to step H);
   G) if not, changing the set of values of the control variables and going back to step D);
   H) if said differences satisfy a refinement criterion, going to step J);
   I) if not, selecting a subset of the network where to calculate predicted values, going back to step D);
   J) classifying an entity of the network to a class in a set of class comprising at least one class representative of a normal state, and at least one class representative of an abnormal state according to the set of control variables as modified in steps C) and G) using a supervised machine learning engine previously trained using historical labeled feature vectors corresponding to said at least one class.

2. The method of claim 1, wherein steps C) to J) are performed for at least one event type, and changing the state of control variables is performed according to said at least one event type.

3. The method of claim 2, wherein a plurality of event types is tested, and one instance of steps C) to J) is performed for each event type.

4. The method of claim 1, wherein the refinement criterion comprises the calculation of values of one of a least square and a Bayesian objective function, and the selection and modification of control variables is determined by a Levenberg-Marquardt algorithm.

5. The method of claim 1, wherein the control variables comprise scalar variables comprising the topology and the topography of the network, and time-based variables comprising the inputs and outputs of the network having at least one value at each time reference.

6. The method of claim 5, wherein changing the set of values of the control variables comprises modifying at least one of:
   the values of a subset of the time-based control variables;
   the values of a subset of the scalar control variables calculated during a phase of modeling of the network.

7. The method of claim 6, wherein modifying the values of a subset of the time-based control variables comprises modifying the values of the time-based control variables representative of water consumption.

8. The method of claim 1, wherein state variables further comprise pressure.

9. The method of claim 1, further comprising classifying the network in a state at the output of:
   J) Classifying an entity of the network in a state according to the set of control variables, and;
   classifying the at least one of a node and an arc of the network based on the comparison of said statistical analysis of residue values with values representative of a behavior of said entity learnt from one or more historical dataset of residue values.

10. A system for detecting anomalies in a water distribution system composed of a network of nodes, said system comprising:
   sensors of at least water velocity and pressure at a subset of nodes of the network;
   a computing device comprising a processor;
   communication links between sensors and the computing device;
   a storage media;
   wherein the computing device is configured for:
      retrieving an initial set of values of control variables comprising the network and its output at the nodes from the storage media and using it to parametrize a hydraulic model of the water distribution system;
      using communication links between sensors on the network to acquire observations of a subset of the state variables, said observations having time references;
   executing a method according to claim 1.

11. A computer program product, stored on a non-transitory computer-readable medium, detecting anomalies in a water distribution system composed of a network of nodes, said computer program product comprising code instructions for executing a method according to claim 1.

12. A method of detecting anomalies in a water distribution system composed of a network of nodes, said method comprising:

parametrizing a hydraulic model of the water distribution system with a set of values of control variables comprising the network and its output at the nodes;

using sensors on the network to acquire observations of a subset of state variables at time references;

using the hydraulic model to calculate predicted values of a set of state variables comprising at least a water velocity at the nodes, said values having time references;

computing residue values of the subset of the state variables as a difference between predicted values and observations at the time references;

performing a statistical analysis of residue values at an entity of the network at a selection of the time references;

classifying the entity of the network based on a comparison of said statistical analysis of residue values with values representative of a behavior of said entity learnt from one or more historical dataset of residue values.

13. The method of claim 12, wherein the statistical analysis comprises the calculation of one of a mean, a standard deviation, an absolute mean or median deviation, an auto-regressive model, boxplot, Support Vector Machine, a Principal Component Analysis (PCA), K-nearest neighbor and results of statistical tests (computing P-values).

14. The method of claim 12, wherein an entity of the network is classified in a class representative of an abnormal state if the residue values at the at least a node exceeds a threshold based on statistical analysis of historical data and operational risk level a predefined number of successive time references.

15. A system for detecting anomalies in a water distribution system composed of a network of nodes, said system comprising:
   sensors of at least water velocity and pressure at a subset of nodes of the network;
   a computing device comprising a processor;
   communication links between sensors and the computing device;
   a storage media;
   wherein the computing device is configured for:
      retrieving an initial set of values of control variables comprising the network and its output at the nodes from the storage media and using it to parametrize a hydraulic model of the water distribution system;
      using communication links between sensors on the network to acquire observations of a subset of the state variables, said observations having time references;
   executing a method according to claim 12.

16. A computer program product, stored on a non-transitory computer-readable medium, detecting anomalies in a water distribution system composed of a network of nodes, said computer program product comprising code instructions for executing a method according to claim 12.

* * * * *